(12) United States Patent
Garratt et al.

(10) Patent No.: US 10,251,721 B2
(45) Date of Patent: Apr. 9, 2019

(54) STORAGE DEVICE FOR MEDICAL EQUIPMENT

(71) Applicants: Daniel Mark Garratt, Stourbridge (GB); Simon Teasdale, Llandew (GB)

(72) Inventors: Daniel Mark Garratt, Stourbridge (GB); Simon Teasdale, Llandew (GB)

(*) Notice: Subject to any disclaimer, the term of this patent is extended or adjusted under 35 U.S.C. 154(b) by 0 days.

(21) Appl. No.: 15/508,566

(22) PCT Filed: Sep. 3, 2015

(86) PCT No.: PCT/GB2015/052545
§ 371 (c)(1),
(2) Date: Mar. 3, 2017

(87) PCT Pub. No.: WO2016/034881
PCT Pub. Date: Mar. 10, 2016

(65) Prior Publication Data
US 2017/0281291 A1   Oct. 5, 2017

(30) Foreign Application Priority Data
Sep. 3, 2014   (GB) .................................. 1415600.4

(51) Int. Cl.
*A61B 50/31* (2016.01)
*A45C 13/02* (2006.01)
(Continued)

(52) U.S. Cl.
CPC .............. *A61B 50/31* (2016.02); *A45C 13/02* (2013.01); *A61B 50/20* (2016.02);
(Continued)

(58) Field of Classification Search
CPC . A45C 13/02; A61B 50/31; A61B 2050/0088; A61B 2050/3011; A61B 2050/314
(Continued)

(56) References Cited

U.S. PATENT DOCUMENTS 4,204,526 A * 5/1980 Samuels ............... A61F 2/0095
383/35
5,052,555 A * 10/1991 Harmon ................. A01K 97/06
190/111
(Continued)

FOREIGN PATENT DOCUMENTS

DE   102007036518   11/2008
EP      2233254 A1    9/2010
(Continued)

*Primary Examiner* — Chun Hoi Cheung
(74) *Attorney, Agent, or Firm* — Dinsmore & Shohl LLP

(57) ABSTRACT

A storage device for carrying medical equipment having an outer shell that is reconfigurable between a closed configuration and an open configuration. The outer shell includes first and second side panels and a fastener is provided for holding the outer shell in the closed configuration. A first support panel has support elements on its inner and outer surfaces for securing medical equipment to the first support panel. In a first configuration the first support panel covers the inner surface of the first side panel and the outer surface of the first support panel is outwardly facing and accessible and the first support panel is pivotable to a second configuration in which the inner surface of the first side panel is uncovered and both the inner surface of the first side panel and the inner surface of the first support panel are outwardly facing and accessible. A second support panel including support elements is secured within the outer shell such that in a first configuration the second support panel covers the inner surface of the second side panel and the outer surface of the second support panel is outwardly facing and accessible, and is pivotable to a second configuration in which the inner surface of the second side panel is uncovered and both the inner surface of the second side panel and the inner surface of the second support panel are outwardly facing and accessible.

14 Claims, 6 Drawing Sheets

(51) Int. Cl.
 *A61B 50/20* (2016.01)
 *A61F 17/00* (2006.01)
 *A61B 50/00* (2016.01)
 *A61B 50/30* (2016.01)
(52) U.S. Cl.
 CPC .............. *A61B 2050/0088* (2016.02); *A61B 2050/3011* (2016.02); *A61B 2050/314* (2016.02); *A61F 17/00* (2013.01)
(58) Field of Classification Search
 USPC .......... 206/570; 190/108–109; 383/35, 61.3, 383/6–31
 See application file for complete search history.

(56) References Cited

U.S. PATENT DOCUMENTS

| | | | | |
|---|---|---|---|---|
| 5,207,303 | A * | 5/1993 | Oswalt | A45C 13/02 190/108 |
| 5,897,209 | A * | 4/1999 | Roegner | A45C 3/00 150/113 |
| 6,109,442 | A * | 8/2000 | Roegner | A45C 11/00 150/106 |
| 6,715,594 | B2 * | 4/2004 | Milionta | A01K 97/06 150/111 |
| 8,272,505 | B2 * | 9/2012 | Melamed | A45C 7/0068 150/113 |
| 9,364,062 | B2 * | 6/2016 | Stukenkemper | A45C 11/34 |
| D790,211 | S * | 6/2017 | Constantini | D3/205 |
| 2006/0072857 | A1 * | 4/2006 | Revels | A45C 3/10 383/35 |
| 2007/0084742 | A1 * | 4/2007 | Miller | A61B 17/3472 206/438 |
| 2008/0121730 | A1 | 5/2008 | Calkin | |
| 2008/0141700 | A1 * | 6/2008 | Fuchs | F25D 3/08 62/371 |
| 2011/0017633 | A1 | 1/2011 | Holstein et al. | |

FOREIGN PATENT DOCUMENTS

| | | |
|---|---|---|
| WO | 9008631 A1 | 8/1990 |
| WO | 9749311 A1 | 12/1997 |

* cited by examiner

STORAGE DEVICE FOR MEDICAL EQUIPMENT

CROSS REFERENCE TO RELATED APPLICATIONS

This application is the U.S. National Phase of international patent application Ser. No. PCT/GB2015/052545, filed Sep. 3, 2015 which claims the benefit of international application Ser. No. GB 1415600.4 filed Sep. 3, 2014, the contents of both of which are incorporated herein in their entirety.

The present invention relates to a storage device for medical equipment, and in particular a bag for carrying emergency medical equipment for use by a medical first responder.

In the event of a casualty in which a person is rendered unconscious and/or experiences serious trauma, the speed of response and actions taken by a first responder will often be critical to the survival and longer term prognosis of the casualty. To ensure that correct and prompt action is taken by a trained first responder, protocols have been developed to ensure that treatment is delivered in an ordered manner in which the most serious threats to life are prioritised. Mnemonics have been developed to assist first responders in the application of these protocols, the most widely used of which is the ABC acronym which stands for Airways, Breathing and Circulation, or variations thereof.

Following the protocol acronym ensures that the functions most vital for life are attended to in the appropriate order. In recent years, it has been recognized that in cases of serious trauma such as massive extremity wounds, the most immediate risk to life is exsanguination. The ABC mnemonic has therefore been modified to CABC, which stands for Catastrophic Bleed, Airway, Breathing, Circulation and Disabilities. In military usage, a similar mnemonic known as MARCH is used to guide tactical medical care. MARCH stands for Massive Haemorrhage, Airway, Respiration, Circulation, Head/Heat/Handling.

In addition to following the correct protocol, it is also important that the first responder is able to access the medical equipment essential for performing each step of the protocol as expediently and efficiently as possible. In the case of massive haemorrhage in particular, a delay in treatment in the order of seconds could result in a fatal level of blood loss. Therefore, time lost attempting to locate a required piece of medical equipment may be critical and could mean the difference between life and death for the casualty. Civilian and military medical first responders are provided with a significant amount of medical equipment to enable them to attend to a wide range of medical emergencies. However, the requirement to carry such a wide range of equipment makes the job of selecting the required piece of equipment at the desired time difficult.

It is therefore desirable to provide an improved storage device for carrying medical equipment which addresses the above described problems and/or which offers improvements generally.

According to the present invention there is provided a storage device for carrying medical equipment as described in the accompanying claims.

In an embodiment of the invention there is provided a storage device for carrying medical equipment comprising an outer shell reconfigurable between a closed configuration and an open configuration, the outer shell including first and second side panels having inner and outer surfaces. A fastener is provided for holding, the outer shell in the closed configuration. A first support panel is provided having inner and outer surfaces each including support elements for securing, medical equipment to the first support panel, the first support panel being secured within the outer shell such that, when the outer shell is open. In a first configuration the first support panel covers the inner surface of the first side panel and the outer surface of the first support panel is outwardly facing and accessible, the first support panel being pivotable to a second configuration in which the inner surface of the first side panel is uncovered and both the inner surface of the first side panel and the inner surface of the first support panel are outwardly facing and accessible. A second support panel is also provide having inner and outer surfaces each including support elements for securing medical equipment to the second support panel, the second support panel being secured within the outer shell such that in a first configuration the second support panel covers the inner surface of the second side panel and the outer surface of the second support panel is outwardly facing and accessible, the second support panel being pivotable to a second configuration in which the inner surface of the second side panel is uncovered and both the inner surface of the second side panel and the inner surface of the second support panel are outwardly facing and accessible. This arrangement advantageously allows medical equipment to be secured within the bag in a manner in which it is readily presented and accessible as soon as the bag is opened. In addition, the arrangement of the support panels is such that the medical equipment may be applied to the panels in such a way that each panel supports a kit of equipment relating to one element of the MARCH or CABC treatment protocol, the panels being selected such that the equipment is presented in a sequence corresponding to the treatment protocol as the panels are reconfigured. It will be appreciated the term "covers" refers to the arrangement in which the panels are facing and adjacent each other, and is not limited to the first and second panels completely covering the respective inner surfaces of the side panels, merely at least partially covering.

Preferably the inner surfaces of the first and second side panels define support panels and include support elements for securing medical equipment to the first and second side panels, thereby ensuring at least 5 separate support panels to correspond to the 5 elements of the treatment protocol.

The first support panel is preferably pivotally secured to the first side panel along one edge, and in the first configuration the inner surface of the first support panels is facing the inner surface of the first side panel and in the second configuration the first support panels and first side panel are side by side. As such the first panel may be provided with bleed kit that is immediately accessible when the bag is opened, and may then be pivoted to reveal the inner surface which may be provided with airway kit.

The second support panel is preferably pivotally secured to the second side panel along one edge, and in the second configuration the inner surface of the second support panel is facing the inner surface of the second side panel and in the second configuration the second support panel and second side panel are side by side.

The first and second support panels are preferably arranged such that when the outer shell is opened both panels are in the first configuration.

The outer shell preferably comprises first and second shell sections hingedly connected along a common edge. The shell sections are substantially identical and symmetrical defining two common halves.

The fastener preferably comprises a zip fastener extending along the open edges of the shell sections, the zip fastener includes two sliders arranged to close the zip from opposing ends in a direction towards each other, the storage device further including a pair of handles secured to shell sections and located on either side of the zip fastener at a common location along the length of the zip, the handles being arranged to enable a person to impart forces in opposing directions away from the zip in a direction transverse to the length of the zip to open the zip when the zip is closed with the sliders both located at a stop position coincident with the handle. This enables the hag to be ripped open in a very rapid manner to access the medical equipment in time critical situations.

The first support panel is preferably located within the first outer shell section and the second support panel is located in the second outer shell section, and in the open configuration the first and second support panels are located on opposing sides of the hinge line of the outer shell and are arranged to pivot away from the hinge line to the second configuration in a direction transverse to the hinge line. Preferably the panels arc elongate and are hinged along, their longest edges.

The first and second support panels preferably include an inner edge arranged adjacent the hinge line of the outer shell, and an opposing outer edge along which the first and second panels are secured to the outer shell.

The support elements are preferably configured to secure the medical apparatus to the support panels such that the apparatus are visible and openly accessible.

At least some of the support elements comprise elastic loops, and others may comprise flexible straps including fastening means such as Velcro®.

In another aspect of the invention there is provided a storage device for carrying medical equipment comprising an outer shell reconfigurable between a closed configuration and an open configuration; a plurality of support surfaces located within the outer shell each including support elements for releasably securing medical apparatus thereto in an openly accessible and releasable manner, the plurality of support surfaces including a first support surface having a kit of bleed equipment secured thereto, a second support surface having a kit of airway equipment secured thereto, a third support surface having a kit of respiratory equipment secured thereto, a fourth support surface having a kit of circulatory equipment secured thereto, and a fifth support surface having at least one of thermal and casualty handling equipment secured thereto. The first support surface is arranged such that it is outwardly facing and the medical kit secured thereto is immediately accessible when the outer shell is opened, and the support surfaces are reconfigurable to enable subsequent sequential access to the second to the fifth support surfaces and the medical kit secured thereto. In this way the equipment is presented to the first responder and is immediately accessible in the sequential order is which it is required, significantly reducing the time taken to access the equipment. In addition, the first responder is prompted as to the order in which treatment should be provided by the order in which the equipment is presented, thereby ensuring protocol is adhered to.

The outer shell preferably includes first and second side panels each having inner surfaces, one of which defines the fifth support surface; a first support panel having an outer surface defining the first support surface and an inner surface defining the second support surface, the first support panel being secured within the outer shell such that, when the outer shell is open, in a first configuration the first support panel covers the inner surface of the first side panel and the outer surface of the first support panel is outwardly facing and accessible, the first support panel being pivotable to a second configuration in which the inner surface of the first side panel is uncovered and both the inner surface of the first side panel and the inner surface of the first support panel are outwardly facing and accessible; and a second support panel having an outer surface defining the third support surface and an inner surface defining the fourth support surface, the second support panel being secured within the outer shell such that in a first configuration the second support panel covers the inner surface of the second side panel and the outer surface of the second support panel is outwardly facing and accessible, the second support panel being pivotable to a second configuration in which the inner surface of the second side panel is uncovered and both the inner surface of the second side panel and the inner surface of the second support panel are outwardly facing and accessible.

The inner surface of the first side panel preferably defines the fifth support surface, and the inner surface of the second side panel defines a six support surface a kit of supplementary circulatory equipment secured thereto in addition to the kit mounted to the fourth support surface.

In a first open configuration the first and third support surfaces are preferably outwardly facing and arranged side by side, in a second configuration the first support surface is pivoted to present the second support surface and uncover the sixth support surface, and in a third open configuration the third support surface is pivoted to present the fourth support surface and uncover the fifth support surface.

In another aspect of the invention there is provided a bag comprising an opening and a fastener for closing the opening, the fastener comprising a zip fastener including two sliders arranged to close the zip from opposing ends in a direction towards each other, the bag further including a pair of handles secured located on either side of the zip fastener at a common location along the length of the zip, the handles being arranged to enable a person to impart forces in opposing directions away from the zip in a direction transverse to the length of the zip to open the zip when the zip is closed with the sliders both located at, a stop position coincident with the handle.

The present invention will now be described by way of example only with reference to the following illustrative figures in which.

Figure 1:
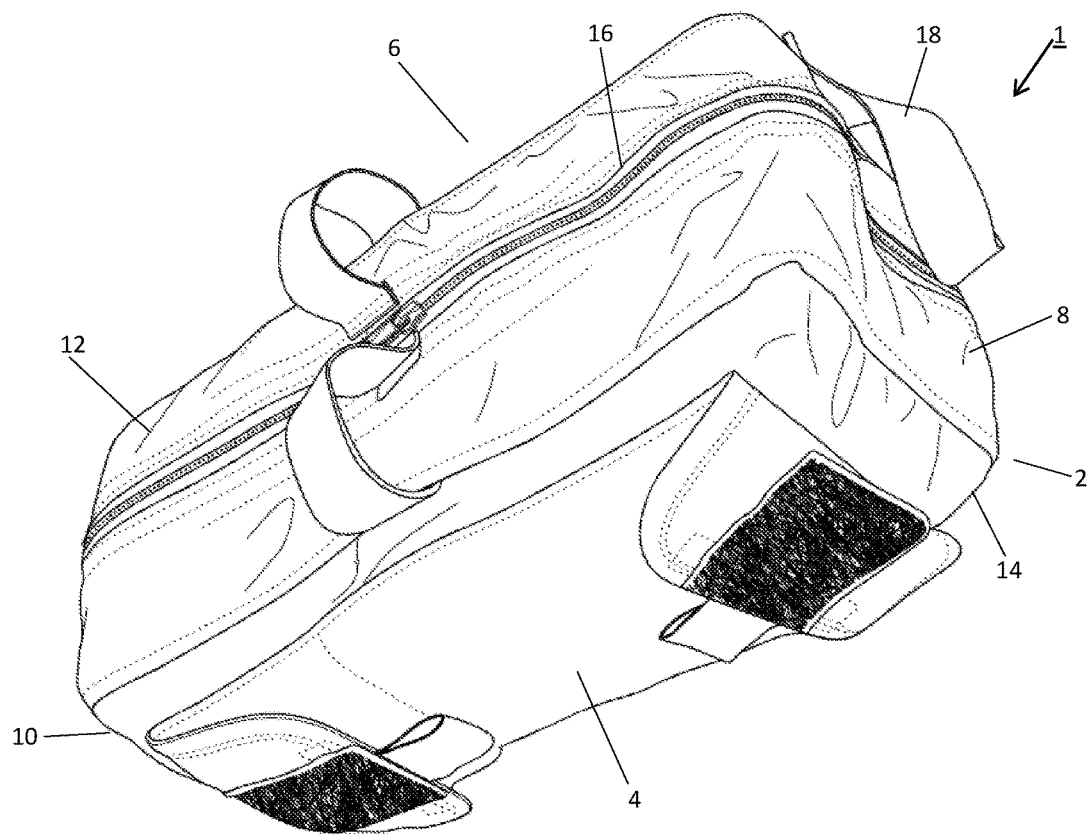
FIG. 1 shows a medical bag according to an embodiment of the invention.

Referring to FIG. 1 there is provided a storage bag 1 for carrying emergency medical equipment. The storage bag 1 comprises an outer shell 2 formed from a heavy duty resilient fabric. The shell 2 forms the outer enclosure of the bag 1. The shell 2 is elongate having first and second sides 4 and 6, first and second ends 8 and 10, an upper panel 12 and a base 14. The shell 2 includes a zip fastener 16 extending longitudinally along the bag, located centrally width-wise, from the base of the first end 8, across the top panel 12 and to the base of the second end 10, dividing the shell into two symmetrical halves. It will however be appreciated that any other suitable fastener, such as Velcro®, clips, hooks or buttons etc. may be utilised. At least one handle 18 is secured to the shell to enable the storage device to be carried by hand.

Figure 2:
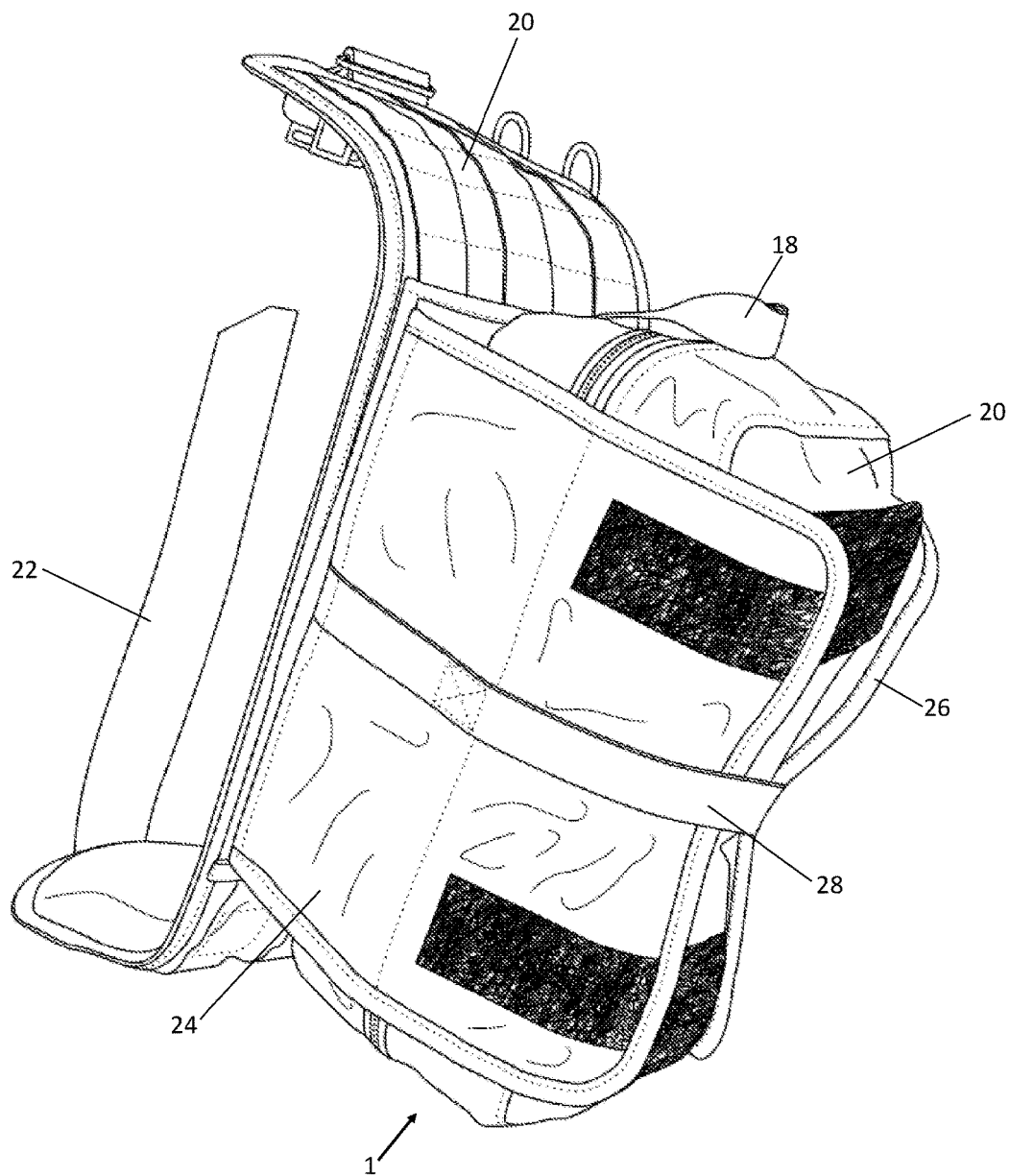
FIG. 2 shows the bag of FIG. 1 secured to a waist belt.

For military applications the bag 1 is configured to be secured to a waist belt 20 as shown in FIG. 2. The waist belt 20 includes a wider padded section for extending around the back and sides of a wearer with a narrower strap 22 at the front for securing the belt in position via a buckle. The belt 20 also includes at the rear an upper panel 24 and lower panel 26. Bag 1 includes a Velcro® panel secured to its rear side face 6 which secures to a corresponding Velcro® panel on the outer face of the belt 20 to secure the bag 1 to the outer surface of the rear part of the belt 20. The upper panel 24 and lower panel 26 extend around the bag when secured in place by the Velcro® and a locking strap 28 secures the upper 24 and lower 26 panels together to surround and hold the bag in securement with the belt 20. In use the clip may be released in a one handed manner to unlock the upper 24 and lower 26 panels to allow release of the bag 1. When the panels are first unlatched the Velcro® is of sufficient strength to hold the bag 1 in position to prevent it falling to the ground. The wearer is then able to reach around and grab the handle 18 to pull the bag 1 away from the Velcro® for use.

Figure 3:
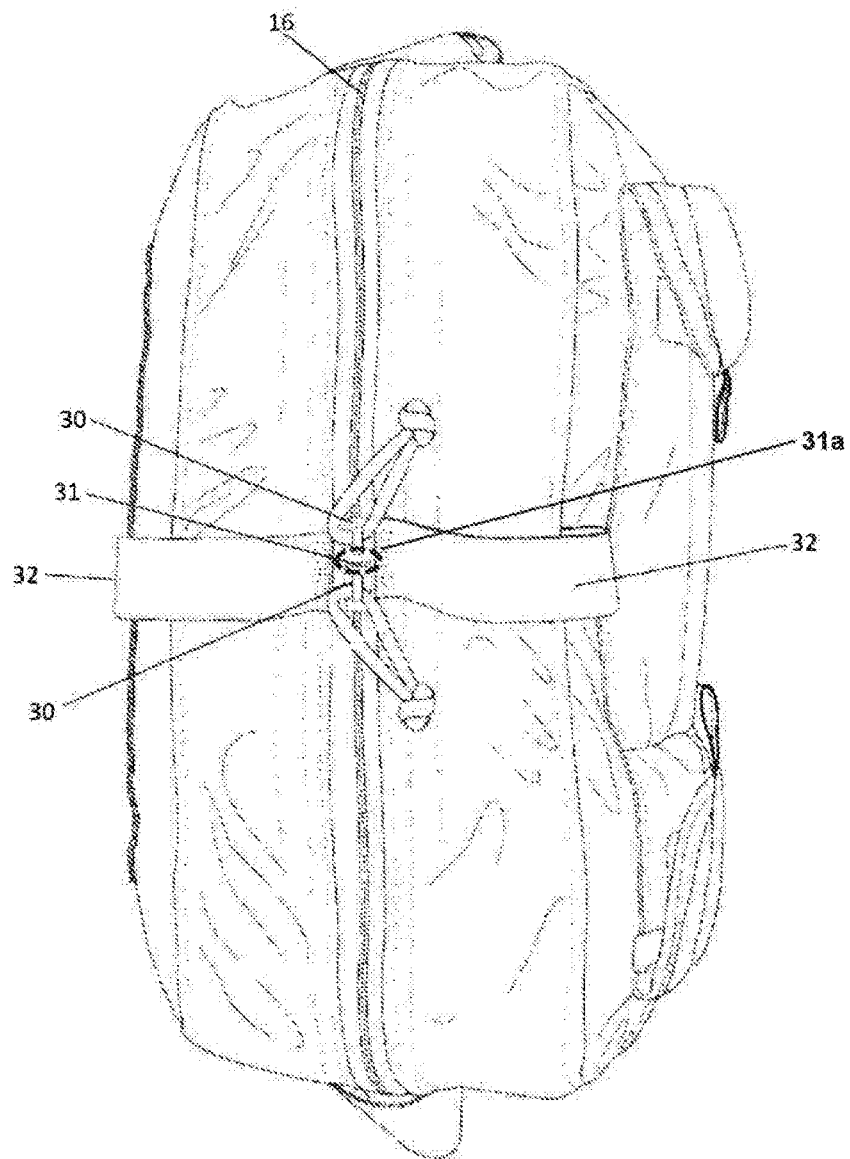
FIG. 3 is a view from above of the medical bag highlighting the zip arrangement.

As shown in FIG. 3, the zip fastener includes two sliders 30 which close the zip fastener from opposing ends in a direction towards the centre of the bag 2. A stop position is defined along the zip fastener 16 at the centre of the top of panel 12. A pair of handles 32 are located longitudinally at the stop position 31 and extend transversely in a perpendicular direction relative to the longitudinal axis defined by the fastener 16. The handles 32 are arranged to be pulled in opposing transverse directions to generate a force perpendicular to the longitudinal opening and closing direction of the zip fastener 16. With the zip fastener 16 closed such that the sliders 30 are located at the stop position 31 adjacent to each other and adjacent the handles 32, an outward transverse force applied in opposing directions to the handles 32 acts to pull the zip fastener 16 apart and slide the sliders 30 in opposing longitudinal direction towards the open position in which they are finally located at the base of the opposing ends 8 and 10. The bag 2 may include stop elements (shown schematically at 31 a) arranged to locate and stop the sliders 30 at the stop position 31. Alternatively, in the absence of stop elements the sliders 30 may be moved to a position in which they are not longitudinally adjacent to the handles 32. In this position any transverse outward force applied to the handles 32 will not open the zip fastener 16. This may be advantageous in certain circumstances where accidental opening of the bag is duly prevented.

Figure 4:
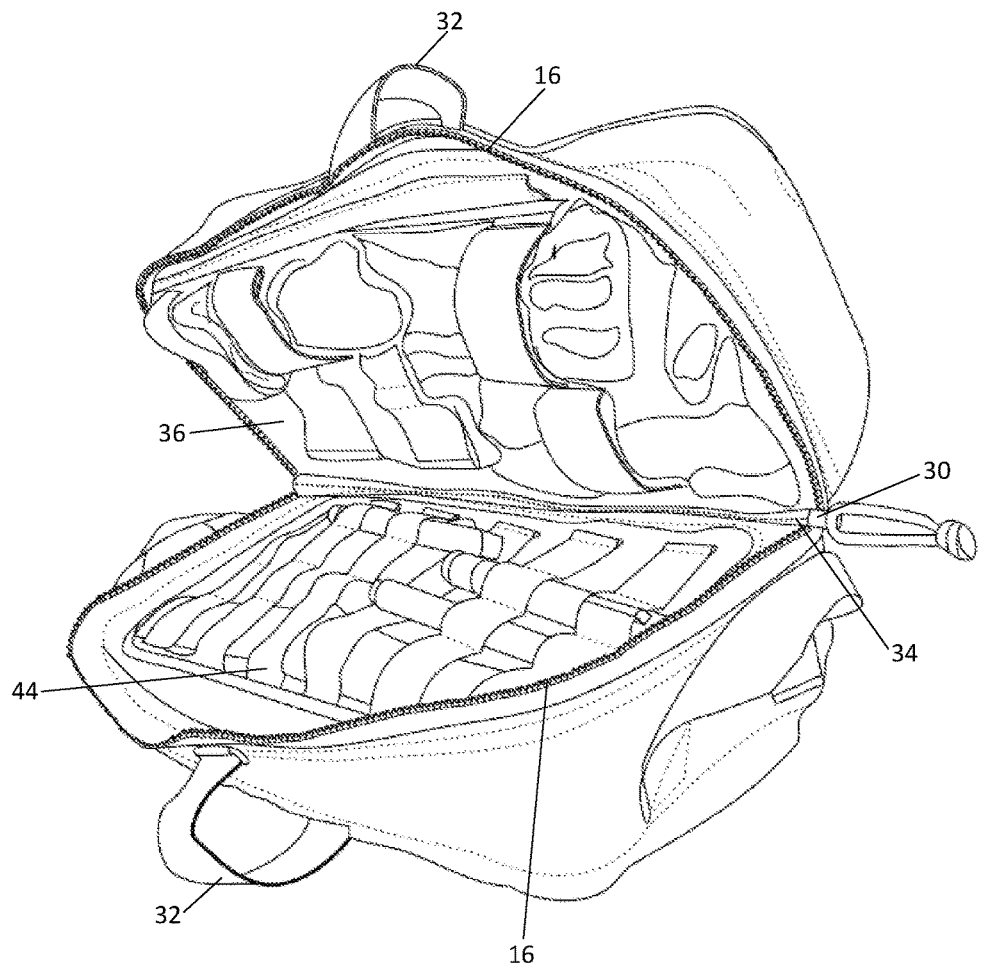
FIG. 4 is a partially open view of the medical bag of the present invention.
Figure 5:
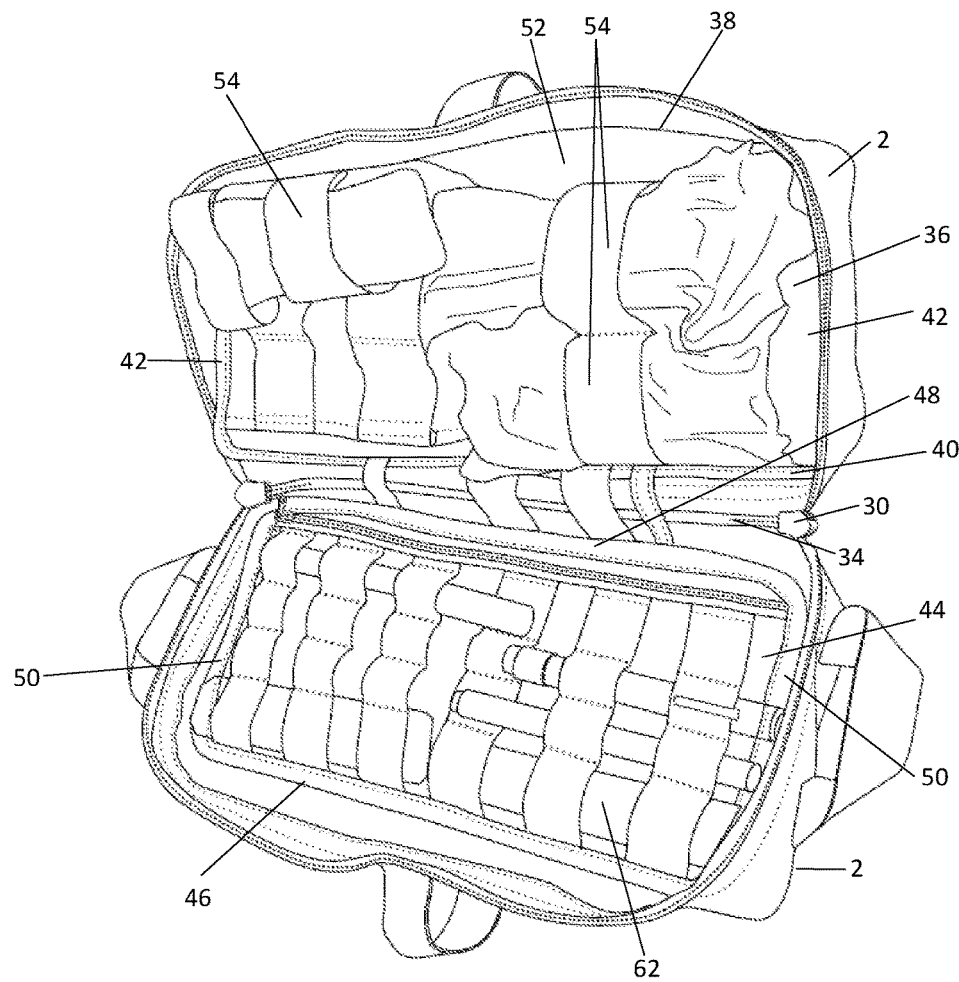
FIG. 5 shows the bag fully open in the first configuration.

As shown in FIG. 4, with the sliders 30 at opposing ends the zip fastener 16 is in the open condition and the halves of the shell 2 are able to be opened in a clam shell manner with a living hinge defined longitudinally along the centre of the base panel 14 which holds the 2 halves together. The two halves are able to pivot about the hinge 34 until they are in a fully open position as shown in FIG. 5 in which the first side 4 and second side 6 are substantially coplanar. In this first open configuration a pair of support panels are exposed. The first support panel 36 includes an outer longitudinal edge 38, an opposing inner longitudinal edge 40 and opposing end edges 42. The first support panel 36 is pivotally secured to the outer shell 2 along its outer longitudinal edge 38 along the inner circuits of the upper panel 12 adjacent to the first side of the zipper fastener 16. The opposing inner longitudinal edge 40 and, end edges 42 are free and not secured to the shell such that the support panel 36 is pivotable relative to the shell 2 about a hinge defined by the connection between the longitudinal edge 38 and the shell 2. The second longitudinal edge 40 is arranged adjacent the edge 34 along the centre of the base panel 14 such that the support panel 36 extends substantially across and covers the inner width of the first half of the shell in the open configuration. A second support panel 44 is also exposed in this first open configuration. The second support panel 44 includes an outer longitudinal edge 46 and inner longitudinal edge 48 with opposing side edges 50 and is secured in the same manner as the first support panel 36 such that it is pivotally secured to the shell 2 along its outer longitudinal edge 46 to define a hinged connection.

The outer facing surface 52 of the first panel 36 is provided with a plurality of securing elements for securing medical equipment to the outer surface 52 of the panel 36. The securing elements are quick release securing elements that securely hold the equipment in position while enabling it to be quickly removed for use. Securing elements may include a combination of elastic straps stitched, bonded or otherwise secured to the upper surface panel 52, Velcro ® straps stitched or otherwise secured to the surface of the panel 52, zip pockets or any other suitable, easily accessible and quickly releasable storage means. In accordance with the CABC and MARCH systems, the first panel 36 includes equipment for treating catastrophic bleeding/massive haemorrhaging. The kit of bleed equipment includes at least one of emergency bandages and tourniquets held in position by elastic strap 64, The positioning of the kit of bleed equipment on the up-surface 52 of the first panel 36 ensures the bleed equipment is immediately accessible and available once the hag is opened to the first open configuration as shown in FIG. 5. Each of the securing elements is configured to hold a single piece of bleed equipment with the straps 54 being arranged adjacent each other in a manner that each piece of equipment is immediately visible and accessible without interference from any other piece of equipment. As such, on opening the hag the user is able to immediately see and access the equipment required for attending to the first element of the treatment protocol relating to catastrophic bleeding. Once catastrophic bleeding has been attended to, and the medic is ready to carry out the next step in the protocol relating to airways, the first panel 36 may be pivoted about the hinged edge 38 to a second open configuration in which the first support panel 36 is pivoted to reveal the lower surface 56, which in the second configuration is upwardly facing with the second support panel 44 remaining in its initial configuration with its upper surface 50 facing outward. This configuration is shown in FIG. 6.

Figure 6:
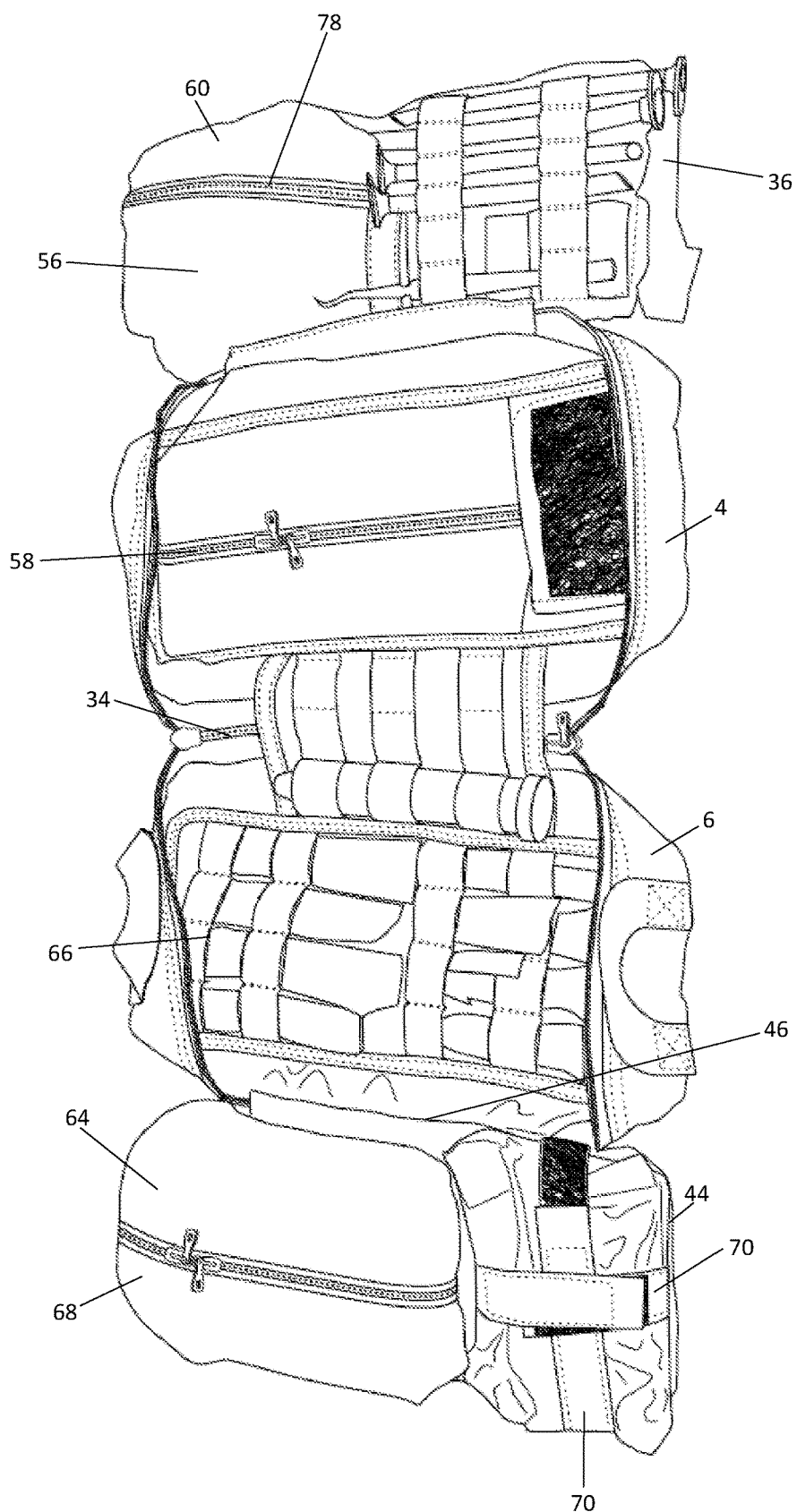
FIG. 6 shows the bag fully open in the third configuration with both support panels folded over.

As shown in FIG. 6, the first panel 36 is pivoted outwardly about the hinged longitudinal edge 38 to a second open configuration in which the outer facing surface 52 of the first panel 36 lies adjacent and coplanar with the outer surface of the side panel 4, with the inner panel 58 being exposed. The inner surface 56 of the support panel 36 includes a kit of airways treatment equipment for tending to the second element of the treatment protocol. Airways equipment includes one or more of nasopharyngeal airways, surgical airways, tracheal hooks, a face shield and lubricating gel. The securing elements for securing this equipment in position on the inner surface 56 of the first panel 36 include elasticated straps stitched to the panel 36 to define loops for holding the airway tubes. A pouch 60 is also provided on the inner surface 56 which is closed by a zip fastener 78 and which contains further breathing equipment. In this second open configuration the massive bleeding equipment on the outer facing surface 52 is secured beneath the now outwardly presented inner surface 56 which is outwardly facing in the second opening configuration.

Having attended to the airways requirement, while still in the second configuration the outer surface 62 of the second panel 44 remains outwardly presented and accessible. The outer surface 62 of the second panel 44 is therefore provided with respiratory equipment for attending to the respiratory needs of a patient once the airways have been treated. The respiratory equipment includes one or more of needle decompressions and chest seals. The respiratory equipment is again held by securing elements which include flexible elastic loops. Once the respiratory needs of the patient have been attended to the second support panel 44 may be pivoted about the hinge line 46 to a third open configuration in which the inner surface of the panel 44 is upwardly presented as shown in FIG. 6.

In the third open configuration both the first panel 36 and second support panel 44 are pivoted outwardly about the respective hinge line in the direction transverse to the longitudinal axis of the bag as defined by the direction of the zip fastener 16. In the third open configuration the inner surface 64 of the second support panel 44 is presented as well as exposing the inner surface 66 of the side panel 6. Both the inner surface 64 and the side panel 6 are provided with a kit of circulation equipment, which includes one or more of syringes, intravenous needles, bags of saline fluid, and saline tubes. The saline fluid is contained within a pouch 68 on the inner surface 64 of the second panel 44 which is formed of a lightweight mesh material having a zip fastener for opening and closing the pouch 68. The saline tube is secured in position by straps 70 which extend in the longitudinal and transverse directions and include Velcro® fasteners for securing them in position around the saline tube and allowing quick release of the same. The needles and other sharps are included in the panel defined by the inner surface of 66 of the side panel 6 held in position by flexible elastic loops. Sharps container 72 is also included for storing used needles in a sanitary manner.

Finally the exposed inner surface 58 of the side panel 4 include storage means for holding aluminium insulation blankets to satisfy the heat requirement of the treatment protocol, as well as casualty cards to assist in the handling of a casualty when responsibility for the treatment is passed from the first responder to a further medical team.

Whilst endeavouring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

The invention claimed is:

1. A storage device for carrying medical equipment comprising:
   an outer shell reconfigurable between a closed configuration and an open configuration, the outer shell including first and second side panels having inner and outer surfaces;
   a first support panel having inner and outer surfaces each including support elements for securing medical equipment to the first support panel, the first support panel being secured within the outer shell such that, when the outer shell is open, in a first configuration the first support panel covers the inner surface of the first side panel and the outer surface of the first support panel is outwardly facing and accessible, the first support panel being pivotable to a second configuration in which the inner surface of the first side panel is uncovered and both the inner surface of the first side panel and the inner surface of the first support panel are outwardly facing and accessible;
   a second support panel having inner and outer surfaces each including support elements for securing medical equipment to the second support panel, the second support panel being secured within the outer shell such that in a first configuration the second support panel covers the inner surface of the second side panel and the outer surface of the second support panel is outwardly facing and accessible, the second support panel being pivotable to a second configuration in which the inner surface of the second side panel is uncovered and both the inner surface of the second side panel and the inner surface of the second support panel are outwardly facing and accessible; and
   a fastener for holding the outer shell in the closed configuration, the fastener comprising a zip fastener extending along the open edges of the shell sections, the zip fastener includes two sliders arranged, to close the zip from opposing ends in a direction towards each other, a stop element arranged to stop the sliders at a stop position along the length of the zip in which the zip is closed and the sliders are adjacent each other, the storage device further including a pair of handles secured to shell sections and located on either side of the zip fastener at the stop position, the handles each having a first end secured adjacent the stop position and being arranged to enable a person to impact forces at a single position along the length of the zip in opposing directions away from the zip transverse to the length of the zip to open the zip when the zip is closed with the sliders both located at the stop position.

2. A storage device according to claim 1 wherein the inner surfaces of the first and second side panels define support panels and include support elements for securing medical equipment to the first and second side panels.

3. A storage device according to claim 1 wherein the first support panel is pivotally secured to the first side panel along one edge, and in the first configuration the inner surface of the first support panels is facing the inner surface of the first side panel and in the second configuration the first support panels and first side panel are side by side.

4. A storage device according to claim 1 wherein the second support panel is pivotally secured to the second side panel along one edge, and wherein in the second configuration the inner surface of the second support panel is facing the inner surface of the second side panel and in the second configuration the second support panel and second side panel are side by side.

5. A storage device according to claim 4 wherein the first and second support panels are arranged such that when the outer shell is opened both panels arc in the first configuration.

6. A storage device according to claim 5 wherein the outer shell comprises first and second shell sections hingedly connected along a common edge.

7. A support device according to claim 6 wherein the first support panel is located within the first outer shell section and the second support panel is located in the second outer shell section, and in the open configuration the first and second support panels are located on opposing side of the hinge line of the outer shell and are arranged to pivot away from the hinge line to the second configuration in a direction transverse to the hinge line.

8. A support device according to claim 7 wherein the first and second support panels include an inner edge arranged adjacent the hinge line of the outer shell, and an opposing outer edge along which the first and second panels are secured to the outer shell.

9. A storage device according to claim 1 wherein the support elements are configured to secure the medical apparatus to the support panels such that the apparatus are visible and openly accessible.

10. A storage device according to claim 5 wherein at least some of the support elements comprise elastic loops.

11. A storage device for carrying medical equipment comprising:
- an outer shell reconfigurable between a closed configuration and an open configuration;
- a plurality of support surfaces located within the outer shell each including support elements for releasably securing medical apparatus thereto in an openly accessible and releasable manner, the plurality of support surfaces including a first support surface having a kit of bleed equipment secured thereto, a second support surface having a kit of airway equipment secured thereto, a third support surface having a kit of respiratory equipment secured thereto, a fourth support surface having a kit of circulatory equipment secured thereto, and a fifth support surface having at least one of thermal and casualty handling equipment secured thereto;
- wherein the first support surface is arranged such that it is outwardly facing and the medical kit secured thereto is immediately accessible when the outer shell is opened, and the support surfaces are reconfigurable to enable subsequent sequential access to the second to the fifth support surfaces and the medical kit secured thereto.

12. A storage device according to claim 11 wherein the outer shell includes first and second side panels each having inner surfaces, one of which defines the fifth support surface;
- a first support panel having an outer surface defining the first support surface and an inner surface defining the second support surface, the first support panel being secured within the outer shell such that, when the outer shell is open, in a first configuration the first support panel covers the inner surface of the first side panel and the outer surface of the first support panel is outwardly facing and accessible, the first support panel being pivotable to a second configuration in which the inner surface of the first side panel is uncovered and both the inner surface of the first side panel and the inner surface of the first support panel are outwardly facing and accessible; and
- a second support panel having an outer surface defining the third support surface and an inner surface defining the fourth support surface, the second support panel being secured within the outer shell such that in a first configuration the second support panel covers the inner surface of the second side panel and the outer surface of the second support panel is outwardly facing and accessible, the second support panel being pivotable to a second configuration in which the inner surface of the second side panel is uncovered and both the inner surface of the second side panel and the inner surface of the second support panel are outwardly facing and accessible.

13. A support device according to claim 12 wherein the inner surface of the first side panel defines the fifth support surface, and the inner surface of the second side panel defines a six support surface a kit of supplementary circulatory equipment secured thereto in addition to the kit mounted to the fourth support surface.

14. A support device according to claim 11 wherein in a first open configuration the first and third support surfaces are outwardly facing and arranged side by side, in a second configuration the first support surface is pivoted to present the second support surface and uncover the sixth support surface, and in a third open configuration the third support surface is pivoted to present the fourth support surface and uncover the fifth support surface.

* * * * *